US012755851B2

(12) United States Patent
Villongco et al.

(10) Patent No.: US 12,755,851 B2
(45) Date of Patent: Oct. 6, 2026

(54) DELIVERY PLAN EVALUATION SYSTEM

(71) Applicant: The Vektor Group, Inc., San Diego, CA (US)

(72) Inventors: Christopher J.T. Villongco, Oakland, CA (US); Maurice J. Pirio, Seattle, WA (US); Marlou Janssen, San Diego, CA (US)

(73) Assignee: THE VEKTOR GROUP, INC., San Diego, CA (US)

( * ) Notice: Subject to any disclaimer, the term of this patent is extended or adjusted under 35 U.S.C. 154(b) by 133 days.

(21) Appl. No.: 18/894,728

(22) Filed: Sep. 24, 2024

(65) Prior Publication Data

US 2025/0246316 A1 Jul. 31, 2025

Related U.S. Application Data

(60) Provisional application No. 63/627,047, filed on Jan. 30, 2024.

(51) Int. Cl.
*G16H 50/50* (2018.01)
*G16H 20/40* (2018.01)

(52) U.S. Cl.
CPC ............ *G16H 50/50* (2018.01); *G16H 20/40* (2018.01)

(58) Field of Classification Search
None
See application file for complete search history.

(56) References Cited

U.S. PATENT DOCUMENTS 6,119,041 A 9/2000 Pomeranz et al.
7,702,495 B2 4/2010 Humphries et al.

(Continued)

FOREIGN PATENT DOCUMENTS

EP 4272678 A1 11/2023
WO WO-2016181317 A2 * 11/2016 ............ G06F 30/20
WO 2021108312 A1 6/2021
WO 2022165245 A1 8/2022
WO 2024154068 A1 7/2024

OTHER PUBLICATIONS

Dosovitskiy, A., et al., An Image is Worth 16X16 Words: Transformers for Image Recognition at Scale, Published as a conference paper at ICLR 2021, 22 pages.
Fayyad, U. M., et al., "On the Handling of Continuous-Valued Attributes in Decision Tree Generation," Machine Learning, 1992, 16 pages, vol. 8, Kluwer Academic Publishers, Boston.

(Continued)

*Primary Examiner* — Lena Najarian
(74) *Attorney, Agent, or Firm* — Ashurst Perkins Coie US LLP

(57) ABSTRACT

System and methods are described for developing a delivery plan for a pulsed field ablation device for treating an arrhythmia. A method runs a lesion development simulation based on cardiac characteristics and a treatment plan that specifies a delivery plan and a target location to generate a simulated lesion having lesion characteristics. The method initializes a three-dimensional (3D) mesh representing a heart based on cardiac characteristics. The vertices of the 3D mesh are associated with cardiac tissue characteristics with some of the associated with cardiac tissue characteristics representing an arrhythmia source. The method adjusts the cardiac tissue characteristics of vertices of the 3D mesh to reflect the effect of an ablation resulting in formation of the simulated lesion. The method runs a lesion evaluation simulation based on the 3D mesh with the adjusted cardiac tissue characteristics to determine whether the simulated lesion would be effective at treating the arrhythmia.

20 Claims, 7 Drawing Sheets

(56) References Cited

U.S. PATENT DOCUMENTS

| | | | | |
|---|---|---|---|---|
| 10,319,144 | B2 | 6/2019 | Krummen et al. | |
| 10,734,096 | B1 | 8/2020 | Neumann | |
| 10,856,816 | B2 | 12/2020 | Villongco | |
| 10,860,754 | B2 | 12/2020 | Villongco | |
| 11,065,060 | B2 | 7/2021 | Villongco | |
| 11,229,478 | B2 | 1/2022 | Howard et al. | |
| 11,259,871 | B2 | 3/2022 | Villongco | |
| 11,896,432 | B2 | 2/2024 | Villongco et al. | |
| 2009/0221999 | A1 | 9/2009 | Shahidi | |
| 2014/0022250 | A1 | 1/2014 | Mansi et al. | |
| 2015/0066818 | A1* | 3/2015 | Choi | A61B 5/7275 706/12 |
| 2016/0022375 | A1* | 1/2016 | Blake | G16H 50/00 600/424 |
| 2017/0027649 | A1 | 2/2017 | Kiraly | |
| 2017/0161896 | A1* | 6/2017 | Blake, III | G06T 7/11 |
| 2017/0220754 | A1 | 8/2017 | Harrah et al. | |
| 2018/0256056 | A1* | 9/2018 | Lu | G09B 23/28 |
| 2020/0022649 | A1 | 1/2020 | Rodriguez | |
| 2020/0060757 | A1 | 2/2020 | Ben-haim et al. | |
| 2020/0069367 | A1* | 3/2020 | Sinnott | A61B 18/16 |
| 2021/0085399 | A1 | 3/2021 | Trayanova | |
| 2021/0137384 | A1 | 5/2021 | Robinson et al. | |
| 2021/0272297 | A1 | 9/2021 | Chen et al. | |
| 2022/0008126 | A1 | 1/2022 | Tsoref et al. | |
| 2022/0061732 | A1* | 3/2022 | Krummen | A61B 5/0036 |
| 2022/0095980 | A1* | 3/2022 | Scharf | A61B 5/367 |
| 2022/0257318 | A1* | 8/2022 | Belalcazar | A61B 18/1206 |
| 2023/0089295 | A1 | 3/2023 | Govari et al. | |
| 2023/0355301 | A1* | 11/2023 | Beckman | A61B 34/10 |
| 2023/0380809 | A1 | 11/2023 | Villongco et al. | |
| 2024/0341852 | A1 | 10/2024 | Villongco et al. | |

OTHER PUBLICATIONS

Krummen, David E., et al. "Rotor stability separates sustained ventricular fibrillation from selfterminating episodes in humans." Journal of the American College of Cardiology 63.24 (2014): 2712-2721.

Villongco, Christopher T., et al. "Patient-specific modeling of ventricular activation pattern using surface ECG-derived vectorcardiogram in bundle branch block." Progress in biophysics and molecular biology 115.2 (2014): 305-313.

Vaswani, A., Shazeer, N., Parmar, N., Uszkoreit, J., Jones, L., Gomez, A.N., Kaiser, Ł. and Polosukhin, I., 2017. Attention is all you need. Advances in neural information processing systems, 30.

Gu, A. and Dao, T., 2023. Mamba: Linear-time sequence modeling with selective state spaces. arXiv preprint arXiv:2312.00752 (Mamba).

International Application No. PCT/US24/40474 entitled "Heart Wall Refinement of Arrhythmia Source Locations" and filed on Aug. 1, 2024.

Gómez-Barea, M., García-Sánchez, T. and Ivorra, A., 2022. A computational comparison of radiofrequency and pulsed field ablation in terms of lesion morphology in the cardiac chamber. Scientific reports, 12(1), p. 16144.

González-Suárez, A., Pérez, J.J., Irastorza, R.M., D'Avila, A. and Berjano, E., 2022. Computer modeling of radiofrequency cardiac ablation: 30 years of bioengineering research. Computer Methods and Programs in Biomedicine, 214, p. 106546.

Meckes, D.,—Computational modeling of electric fields for lesion depth analysis. Heart Rhythm O2, 3(4), pp. 433-440.

Potse, M., Dubé, B., Richer, J., Vinet, A., & Gulrajani, R., 2006. A Comparison of Monodomain and Bidomain Reaction-Diffusion Models for Action Potential Propagation in the Human Heart. IEEE Transactions on Biomedical Engineering, 53, pp. 2425-2435.

Villongco, C.T., 2015. Patient-specific Computational Models of Dyssynchronous Heart Failure and Cardiac Resynchronization Therapy for Clinical Diagnosis and Decision Support. University of California, San Diego.

U.S. Appl. No. 63/550,020 titled "Cardiac Catheter Path Planning System" and filed Feb. 5, 2024.

International Search Report and Written Opinion received for Application No. PCT/US24/23763, mailed on Sep. 19, 2024, 18 pages.

Arena et al., "High-frequency irreversible electroporation (H-FIRE) for non-thermal ablation without muscle contraction," BioMedical Engineering OnLine, Nov. 21, 2011, 21 pages.

Baena-Montes et al., "Electroporation Parameters for Human Cardiomyocyte Ablation In Vitro," Journal of Cardiovascular Development and Disease, Jul. 28, 2022, 12 pages.

Berjano, "Theoretical modeling for radiofrequency ablation: state-of-the-art and challenges for the future," BioMedical Engineering OnLine, Apr. 18, 2006, 17 pages.

Bradley et al., "Pulsed field ablation for pulmonary vein isolation in the treatment of atrial fibrillation," J Cardiovasc Electrophysiol, Aug. 31, 2020, 12 pages.

Futyma et al., "Bipolar Endo-Epicardial Radiofrequency Ablation of Arrhythmia Originating From the Left Ventricular Summit," Circ J., May 25, 2018, 2 pages.

González-Suárez, et al., "Computer modeling of radiofrequency cardiac ablation: 30 years of bioengineering research," vol. 214, 2022, 106546, ISSN 0169-2607, https://doi.org/10.1016/j.cmpb.2021.106546.

Gomez-Barea et al., "A computational comparison of radiofrequency and pulsed field ablation in terms of lesion morphology in the cardiac chamber," Scientific Reports, Sep. 27, 2022, 16 pages.

Izquierdo et al., "Endo-epicardial versus only-endocardial ablation as a first line strategy for the treatment of ventricular tachycardia in patients with ischemic heart disease," Circulation: Arrhythmia and Electrophysiology, Aug. 8, 2015, 8 pages.

Ji et al., "The Effect of Discharge Mode on the Distribution of Myocardial Pulsed Electric Field—A Simulation Study for Pulsed Field Ablation of Atrial Fibrillation," Journal of Cardiovascular Development and Disease, Mar. 2, 2022, 13 pages.

Maor, "Fundamental study on the effects of irreversible electroporation pulses on blood vessels with application to medical treatment," University of California, Berkeley ProQuest Dissertations & Theses, 2009, 184 pages.

Meckes, Supplement, Medtronic, 7 pages.

Kotnik et al., "Theoretical Evaluation of Voltage Inducement on Internal Membranes of Biological Cells Exposed to Electric Fields," Biophysical Journal, vol. 90, Jan. 15, 2006, pp. 480-491.

Nakagawa et al., "Effects of Contact Force on Lesion Size During Pulsed Field Ablation," Heart Rhythm, vol. 18, Issue No. 8, August Supplement 2021, S242-S243, 2 pages.

Patel, "Pulsed Field Ablation for Atrial Fibrillation: Recent Advances and Future Directions," EP Lab Digest, 2023, 6 pages.

Perez et al., "How intramyocardial fat can alter the electric field distribution during Pulsed Field Ablation (PFA): Qualitative findings from computer modeling," PLOS One, Nov. 2, 2023, 15 pages.

Simon et al., "Toward a Quasi-dynamic Pulsed Field Electroporation Numerical Model for Cardiac Ablation: Predicting Tissue Conductance Changes and Ablation Lesion Patterns," Computing in Cardiology, 2022, vol. 49, 4 pages.

Singh et al., "Thermal Ablation of Biological Tissues in Disease Treatment: A Review of Computational Models and Future Directions," Electromagnetic Biology and Medicine, vol. 39, 2020, pp. 49-88.

Soucek et al., "Use of Bipolar Radiofrequency Catheter Ablation in the Treatment of Cardiac Arrhythmias," Current Cardiology Reviews, May 22, 2018, 7 pages.

Verma et al., "Effects of Tissue Proximity on Cardiac Lesion Formation Using Pulsed Field Ablation," Heart Rhythm, vol. 19, Issue No. 5, May Supplement 2022, S228, 1 page.

Wang et al., "Cardiac Radiofrequency Ablation Simulation Using a 3D-Printed Bi-Atrial Thermochromic Model," Applied Sciences, Jun. 28, 2022, 12(13), 6553, 14 pages.

Zang et al., "Comparative Analysis of Temperature Rise between Convective Heat Transfer Method and Computational Fluid Dynamics Method in an Anatomy-Based Left Atrium Model during Pulsed Field Ablation: A Computational Study," Journal of Cardiovascular Development and Disease, Jan. 30, 2023, 22 pages.

(56) References Cited

OTHER PUBLICATIONS

International Search Report and Written Opinion received in Application No. PCT/US25/13820, dated Mar. 26, 2025, 15 pages.
Ashikaga et al. "Feasibility of image-based simulation to estimate ablation target in human ventricular arrhythmia." Heart Rhythm 10.8 (2014 ): 1109-1116. Retrieved on Mar. 11, 2025, 16 pages.

* cited by examiner

DELIVERY PLAN EVALUATION SYSTEM

CROSS-REFERENCE TO RELATED APPLICATIONS

This application claims the benefit of U.S. Provisional Application No. 63/627,047, filed on Jan. 30, 2024, which is hereby incorporated by reference in its entirety.

BACKGROUND

Many heart disorders can cause symptoms, morbidity (e.g., syncope or stroke), and mortality. Common heart disorders caused by arrhythmias include inappropriate sinus tachycardia (IST), ectopic atrial rhythm, junctional rhythm, ventricular escape rhythm, atrial fibrillation (AF), ventricular fibrillation (VF), focal atrial tachycardia (focal AT), atrial microreentry, ventricular tachycardia (VT), atrial flutter (AFL), premature ventricular complexes (PVCs), premature atrial complexes (PACs), atrioventricular nodal reentrant tachycardia (AVNRT), atrioventricular reentrant tachycardia (AVRT), permanent junctional reciprocating tachycardia (PJRT), and junctional tachycardia (JT). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant arrhythmia episodes. Arrhythmias can be treated with an ablation by targeting the source of the heart disorder. Ablation technologies include pulsed field ablation (PFA), radiofrequency energy ablation (RFA), other electromagnetic energy ablation, cryoablation, ultrasound ablation, laser ablation, external radiation sources, and so on.

PFA employs non-thermal energy to destroy cellular tissue. PFA destroys cells using electrical pulses by causing the cell membranes to develop permanent pores, leading to cell death in a process referred to as irreversible electroporation (IRE). PFA may be employed in a cardiac ablation procedure to treat an arrhythmia. An arrhythmia may be caused by malfunctioning cardiac tissue that results in abnormal activation of tissue. The goal of an ablation procedure is to destroy tissue so that normal sinus rhythm is restored thus terminating the arrhythmia. The tissue to be destroyed is the target of the ablation procedure. The target may be the malfunctioning tissue (referred to as the source of the arrhythmia) so that the tissue can no longer initiate abnormal activation. The target may also be healthy tissue that is near the source to effectively isolate the effects of the abnormal activation so that the activation cannot spread through the ablated tissue to other healthy tissue. A pulmonary vein isolation (PVI) is a type of ablation that isolates the effects of the abnormal activation.

PFA devices provide a variety of controllable configuration parameters that specify the operation of the PFA device. Although the parameters that can be configured are dependent on the type of PFA device, the parameters may include pulse amplitude (voltage), pulse duration, pulse frequency, pulse shape (e.g., monophasic or biphasic), electrode configuration, and energy delivery mode (e.g., single, burst, or continuous). The settings for the values of the parameters may be referred to as an activation plan. However, because there may be a large number of parameters and settings that are available for each parameters, the number of possible activation plans may be very large.

When planning for an ablation procedure, an activation plan is developed with the goal to ablate only the tissue that is needed to terminate the arrhythmia in as short a procedure time as reasonable. However, current approaches for performing a PFA ablation rely primarily on a physician's experience in developing an activation plan. Such an activation plan may not be optimal especially given the large number of possible activation plans. Although an activation plan could be modified during an ablation procedure, such a modification may also not be optimal.

Some techniques have been proposed for modeling the characteristics of a lesion resulting from a PFA ablation given a set of configuration parameters. Although such techniques may be helpful to a physician in deciding on a treatment plan, they do not assess whether the resulting lesion would result in terminating the arrhythmia.

DETAILED DESCRIPTION

Figure 1:
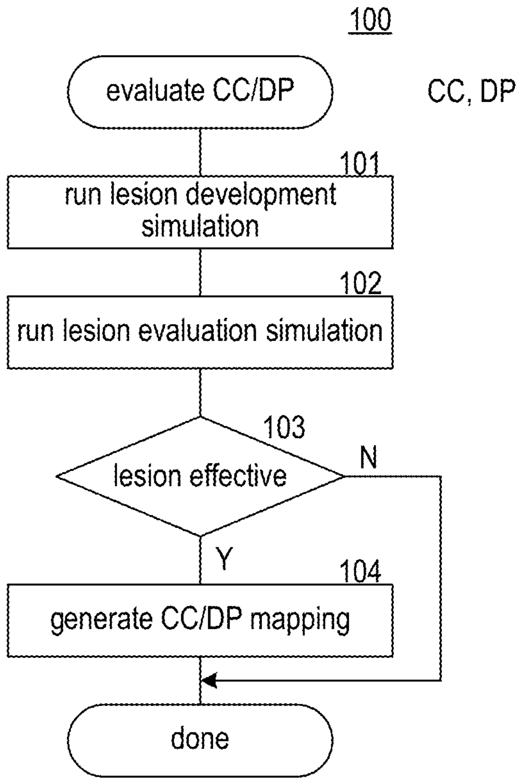
FIG. 1 is a flow diagram that illustrates the processing of an evaluate CC/DP component in some embodiments.

A planning system is provided that identifies a treatment plan for a patient based on modeling development of a lesion and evaluating (assessing) whether that lesion would be effective in treating the patient's arrhythmia. The planning system may include a PFA planning system and a RFA planning system. Although the planning system is described primarily in the context of PFA planning, the modeling and evaluating may be performed in an analogous manner for RFA planning. The PFA planning system may be employed to generate a library of treatment plans that are mapped to cardiac characteristics (e.g., wall thickness) for which the treatments would be effective. Given the cardiac characteristics of a patient, the PFA system identifies one or more treatment plans that are likely to be effective at treating the arrhythmia. The PFA planning system may also be employed during an ablation procedure to model development of a lesion based on data collected during the ablation procedure and evaluate whether that lesion would likely be effective at treating the arrhythmia.

A treatment plan for a patient may specify an ablation technology, a delivery plan (DP), and a target location. The DPs are ablation technology dependent. For example, a DP for PFA technology specifies PFA parameters such as ablation technology (e.g., PFA or RFA), catheter type (e.g., lasso, flower, focal, basket), electrode configuration (e.g., unipolar or bipolar), waveform of electrical pulses (e.g., monophasic or biphasic), and an electrode activation plan for each electrode. The catheter type may be, for example, a lasso catheter with nine electrodes, a 25 mm diameter loop, and a 9 Fr shaft. An electrode activation plan specifies a duration and voltage for each time interval of an activation duration. An electrode activation plan may be represented as a sequence of voltages and a voltage duration for each voltage. For example, an electrode activation plan may be specified as a sequence of a number of cycles (e.g., 50), cycle characteristics, and an inter-cycle duration (e.g., 10 μs) of 0. Cycle characteristics for a monophasic PFA may be specified as voltage and duration, for example, 1000V and 100 μs. Cycle characteristics for a biphasic PFA may be specified as voltage, duration, and inter-phase delay, for example, 1000V, 100 μs, and 10 μs, which means 1000V for 100 μs, 0V for 10 s, 1000V for 100 μs, and so on. The DP may also specify electrode positioning relative to the target location including orientation of the catheter (e.g., angle relative to the heart wall), distance from or depth within the heart wall, contact force, and so on.

A target location of a treatment plan indicates a location where the catheter is to be positioned when an ablation is performed based on a DP. The target location may be endocardial, myocardial, or epicardial and may be determined in various ways. A mapping system may be employed to determine a target location based on a cardiogram (CG), such as an electrocardiogram (ECG) or a vectorcardiogram (VCG), collected from the patient. A mapping system is described in U.S. Pat. No. 10,856,816 titled "Machine Learning Using Simulated Cardiograms" and issued on Dec. 8, 2020, which is hereby incorporated by reference. Such a mapping system identifies a source location of an arrhythmia which may be the target location. A mapping system may identify a source location that is endocardial and then refine the source location to a depth within the myocardium using techniques described in PCT App. No. PCT/US24/40474 entitled "Heart Wall Refinement of Arrhythmia Source Locations" and filed on Aug. 1, 2024, which is hereby incorporated by reference. A target location may also be specified manually by a person.

A treatment plan may specify a sequence of target locations and a DP plan. For example, a person may specify a desired ablation pattern for an ablation such as an ablation line to isolate an arrhythmia relating to a pulmonary vein. Alternatively, an ablation pattern may be identified based on simulations of electrical activity assuming ablation patterns. Techniques for determining an ablation pattern are described in U.S. Pat. No. 11,065,060 titled "Identify Ablation Pattern for Use in An Ablation" and issued on Jul. 20, 2021, which is hereby incorporated by reference. The ablation line and ablation pattern may be subdivided into target locations and DP may be identified for each target location. Thus, a treatment plan may also specify different DPs for different target locations of a treatment plan.

Several models have been developed to estimate lesion development for a DP for PFA and RFA. The models for PFA are based primarily on electroporation of cardiac cells (e.g., effects on transmembrane potential) resulting from the electric field generated by a delivery plan. The models for RFA are based primarily on heat generated by the radiation. The models may also factor in the cooling effects of blood flow within a cardiac chamber and, for PFA, heating effects on blood within the heart wall. Models for both PFA and RFA are described in (A) Gómez-Barea, M., García-Sanchez, T. and Ivorra, A., 2022. A computational comparison of radiofrequency and pulsed field ablation in terms of lesion morphology in the cardiac chamber. *Scientific reports,* 12 (1), p. 16144; (B) González-Suárez, A., Pérez, J. J., Irastorza, R. M., D'Avila, A. and Berjano, E., 2022. Computer modeling of radiofrequency cardiac ablation: 30 years of bioengineering research. *Computer Methods and Programs in Biomedicine,* 214, p. 106546; and (C) Meckes, D.,-Computational modeling of electric fields for lesion depth analysis. *Heart Rhythm* O2, 3 (4), pp. 433-440, which are hereby incorporated by reference.

As discussed above, the techniques described herein can be applied to RFA technology. The primary difference is that the PFA and RFA have different models for lesion development (as described in the above references) and have different controllable (and non-controllable) configuration parameters. Some ablation devices support both PFA technology and RFA technology. During a single procedure with such an ablation device, PFA technology may be employed to create a lesion at one target location, and RFA technology may be employed to create a lesion at another target location. The techniques described herein may be employed to identify a combined DP that employs both PFA and RFA to create a lesion at a single target location.

The PFA planning system evaluates the effect of a DP on a heart having a specified set of cardiac characteristics (CC set). The PFA planning system simulates lesion development (also referred to as modeling lesion development) based on the DP and the CC set to generate lesion characteristics of a lesion that would result from the DP. The PFA planning system then evaluates the effects that the lesion would have on a heart having the CC set. To evaluate the effects, the PFA planning system simulates electrical activity of a heart that has both the lesion and the CC set. If the simulation indicates that cardiac electrical activity of a heart with the CC set would be improved with the lesion (e.g., satisfies a lesion effectiveness criterion), the PFA planning system indicates that the lesion may be an effective treatment. For example, if the CC set represents a heart with an arrhythmia, the lesion may be considered effective if it would terminate, suppress, or increase the arrhythmia induction threshold for the arrhythmia.

The PFA planning system runs lesion development simulations based on simulated CC sets and simulated DPs. A CC set includes cardiac geometry (e.g., atrial dimensions, atrial wall thickness, and cardiac orientation), tissue state (e.g., healthy, borderzone, and scar), tissue conductivity (e.g., normal, slow, and conduction block that are determined based on action potential velocity), source location, a heart scan, and so on. A lesion development simulation may employ a three-dimensional (3D) mesh based on cardiac geometry with parameters associated with the vertices initialized based on the tissue state and tissue conductivity. The 3D mesh may only represent the region of the heart in which the lesion is likely to develop. For each simulation interval, the cellular effect of the DP (e.g., electroporation) is updated for each vertex based on the prior simulation interval and the electrode activation(s) for the current simulation interval. The tissue state associated with vertices near the electrodes will transition from no electroporation (NE) to reversible electroporation (RE) to irreversible electroporation (IRE). IRE indicates that the myocardial tissue will undergo apoptosis and become part of the durable lesion. The electroporation state of the vertices defines the volumes that represent NE, RE, and IRE. The PFA planning system may also run a lesion development simulation for a DP specified by a person (e.g., physician).

After the lesion development simulation is run, the PFA planning system runs a lesion evaluation simulation based on the CC set and the lesion (i.e., lesion characteristics) to determine the effectiveness of the lesion. The PFA planning system initializes a 3D mesh based on the CC set and the lesion characteristics. The lesion characteristics may include, for each tissue state, a delineation of the volume(s)

that have that tissue state. The 3D mesh may represent, for example, an atrium or a ventricle. The PFA planning system runs the lesion evaluation simulation to simulate cardiac electrical activity. Techniques for simulating cardiac electrical activity are described in (1) Henriquez, C. S., 1993. Simulating the electrical behavior of cardiac tissue using the bidomain model. *Critical reviews in biomedical engineering,* 21(1), pp. 1-77, (2) Potse, M., Dubé, B., Richer, J., Vinet, A., & Gulrajani, R., 2006. A Comparison of Monodomain and Bidomain Reaction-Diffusion Models for Action Potential Propagation in the Human Heart. *IEEE Transactions on Biomedical Engineering,* 53, pp. 2425-2435, and (3) Villongco, C. T., 2015. *Patient-specific Computational Models of Dyssynchronous Heart Failure and Cardiac Resynchronization Therapy for Clinical Diagnosis and Decision Support*. University of California, San Diego, which are hereby incorporated by reference. The PFA planning system may run until the electrical activity stabilizes or until some other criterion is satisfied (e.g., maximum number of simulation intervals). A technique for determining stabilization is described in Krummen, D. E., Hayase, J., Morris, D. J., Ho, J., Smetak, M. R., Clopton, P., Rappel, W. J. and Narayan, S. M., 2014. Rotor stability separates sustained ventricular fibrillation from self-terminating episodes in humans. Journal of the American College of Cardiology, 63 (24), pp. 2712-2721, which is hereby incorporated by reference. If the electrical activity stabilizes, the PFA planning system evaluates whether the lesion would be effective at treating the arrhythmia based on various factors such as absence of an arrhythmia, delayed onset of the arrhythmia, and so on. If the electrical activity does not stabilize or stabilizes in an arrhythmia, the lesion may be considered to be not effective.

The PFA planning system may also run lesion evaluation simulations for lesions specified by a person. The PFA planning system may provide a user interface that displays a 3D graphic of a heart along with a 3D object (e.g., sphere) that represents the lesion. The person may move the 3D object to a desired position in the myocardium. The person may deform the 3D object to designate a lesion geometry. As the 3D object is deformed, the endocardium and epicardium may be shown to illustrate the lesion geometry relative to the endocardium and epicardium. As described below, the 3D graphic may be rotated in any direction to help designate and visualize the lesion geometry. The initial 3D object that is displayed may be based on a lesion that is generated by a lesion development simulation. A person may want to deform that lesion to evaluate the effectiveness of variations of that lesion.

In some embodiments, the PFA planning system may identify a DP that would result in development of an effective lesion based on a patient-specific CC set. In such an embodiment, the PFA planning system may run patient-specific lesion development simulations for various DPs and then run patient-specific lesion evaluation simulations based on the lesions to identify one or more DPs that may be effective. The PFA planning system may also run a patient-specific lesion development simulation for a DP specified by a person (e.g., physician).

In some embodiments, the PFA planning system generates a DP library with mappings of CC sets to DPs that would result in the development of lesions that would be effective for the CC sets. To generate the DP library, the PFA planning system may run a lesion development simulation and a lesion evaluation simulation for each combination of a DP and a CC set. Because the computational complexity of running both simulations for each combination may be high, the PFA planning system may employ various techniques to reduce the computational complexity. The PFA planning system may generate clusters of similar CC sets. Since the CC sets of a cluster are similar, a DP likely has a similar effectiveness for each CC set of the cluster. For example, the PFA planning system may generate clusters of CC sets that have similar CCs (satisfy a CC similarity criterion) near an ablation target and, for each cluster, run only one lesion development simulation for each DP. The CCs that are not near the ablation target may have very little (if any) impact on lesion development. As another example, the PFA planning system may generate clusters of overall similar CC sets (not limited to near the target location) and, for each DP, run only one lesion evaluation simulation for a cluster.

The PFA planning system may also employ various bootstrapping techniques to reduce the computational complexity of running the simulations. For example, the initial portion of a DP may be similar (satisfy an initial portion similarity criterion) to the initial portion of many other DPs. In such a case, the PFA planning system may run a bootstrapping lesion development simulation for the initial portion of one DP to generate a bootstrapping lesion. For the other DPs, the PFA planning system initializes a bootstrapped lesion development simulation based on the bootstrapping lesion and runs the bootstrapped lesion development simulation for the remainder of that DP to generate a bootstrapped lesion. The remainder of a DP is the portion of that DP that is after the similar initial portion. As another example, the PFA planning system may run a bootstrapping lesion evaluation simulation for one lesion and CC set to generate bootstrapping voltage solutions for simulation intervals. The PFA planning system then initializes a bootstrapped voltage solution of a bootstrapped lesion evaluation simulation with a similar lesion and CC set to the bootstrapping voltage solution. The PFA planning system then runs the bootstrapped lesion evaluation simulation. The bootstrapped lesion evaluation simulation is likely to stabilize faster than if initialized (for regions outside of the lesion) to random or default values.

In some embodiments, the PFA planning system may run a lesion development simulation in development intervals (also referred to as steps) and run a lesion evaluation simulation after some number of development intervals referred to as an evaluation interval. This allows for various initial portions of a DP to be evaluated to determine whether just an initial portion may be effective. At each evaluation interval, the PFA planning system runs a lesion evaluation simulation based on the lesion that has developed so far. If the lesion is determined to be effective for a CC set, then that portion of the DP is associated with that CC set and the lesion development simulation is terminated. Otherwise, the PFA planning system continues the lesion development simulation. For example, if a DP specifies 50 cycles of 1000V for 100 us with an inter-cycle duration of 10 us and the evaluation intervals are every 10 cycles, the PFA planning system would run between one and five lesion evaluation simulations. The incremental running of a lesion development simulation tends to identify the minimum initial portion of a DP that will be effective for a CC set. An PFA based on this initial portion is likely to result in an effective lesion that is smaller than a lesion generated based on the entire DP. An DP may also specify multiple electrode activation plans that may be performed sequentially such as one electrode activation plan that is to be followed by a different electrode activation plan. To support multiple activation plans, the PFA system may run lesion development simulations for different combinations of electrode activation plans.

When a treatment plan specifies multiple target locations, the PFA planning system may run lesion development simulations for each target location. Since no simulated lesion for a single target location may be effective at termination the arrhythmia, the PFA planning system may interleave the running the lesion development simulations. The PFA planning system may run some number of simulation intervals for each target location and then run a lesion evaluation simulation based on the combination of lesions that have been developed. If the lesions are determined to be not effective, the PFA planning system then continues the lesion development simulations. The PFA planning system may also run lesion development simulations for subsets of the target locations and run lesion evaluation simulations for each subset to identify subsets that may be effective. The PFA planning system may employ a different electrode activation plan for each target location.

The simulations used to generate the library may be based on CC sets that are considered to be arrhythmic and the CC sets may be clinical (e.g., based on electronic health records) and/or simulated. Techniques for generating simulated CC sets are described in U.S. Pat. No. 10,860,754 titled "Calibration of Simulated Cardiograms" and issued on Dec. 8, 2020, which is hereby incorporated by reference. The '754 patent also describes running arrhythmia simulations based on a CC set. If an arrhythmia simulation for a CC set results in development of an arrhythmia, then the PFA planning system may include that CC set in a collection of CC sets whose DPs are to be determined. To determine the DP for such a CC set, the FPA planning system may initialize the parameters of the 3D mesh for the lesion evaluation simulation to parameters of the 3D mesh of the arrhythmia simulation except for the parameters of vertices within the lesion which are set to values to reflect the lesion such as setting the action potential velocity to zero.

In some embodiments, the PFA planning system may generate a simulated cardiogram (CG), such as an electrocardiogram (ECG) or a vectorcardiogram (VCG), for an arrhythmia simulation based on a CC set. The PFA planning system may add the cardiogram to the mapping of the CC set to a DP that is stored in the DP library. The DP library may contain mappings of a CC set and/or CG to a DP.

To determine a DP for a patient, the PFA planning system identifies from the DP library a mapping that includes a CC set (or any subset of the CC set) that is similar (based on a CC similarity criterion) to the patient CC set (or any subset of the patient CC set). The DP associated with that mapping may be considered to be effective in treating the patient. The PFA planning system may identify the patient tissue state and source location of the patient CC set using the technology described in '754 patent and in U.S. Pat. No. 11,896,432 titled "Machine Learning for Identifying Characteristics of a Reentrant Circuit" and issued on Feb. 13, 2024, which is hereby incorporated by reference. The PFA planning system may identify the depth of a source location using the technology described in PCT App. No. US2024/040474 titled "Heart Wall Refinement of Arrhythmia Source Locations" and filed on Aug. 1, 2024, which is hereby incorporated by reference. The determination of a DP for a patient may also factor in other criteria when identifying DP for a patient such as closeness to an avoidance structure (e.g., phrenic nerve, coronary artery, and esophagus), lesion geometry, and so on. Even though a DP may be determined to be effective, the closeness of the resulting lesion to an avoidance structure may make an ablation based on that DP too risky. Also, the extent of the lesion may make an ablation based on that DP not advisable given various cardiac characteristics such as the extent of another lesion or other scar tissue.

The PFA planning system may alternatively identify a mapping that includes a CG that is similar (based on a CG similarity criterion) to a patient CG of a patient. The DP associated with that mapping may be considered effective in treating the patient. The PFA planning system may also identify a mapping that includes both a CC set and a CG that are similar (based on a CC/CG similarity criterion) to the patient CC set and the patient CG.

The PFA planning system may identify a DP based on target lesion characteristics. A person may manually specify a target lesion (e.g., draw the lesion geometry and specify other lesion characteristics such as scar and borderzone tissue). The PFA planning system then identifies, from the DP library, mappings with lesions that are similar (based on a lesion similarity criterion) to the target lesion and with CC sets that are similar to the patient CC set. Lesion similarity may be based on a lesion similarity criterion. Lesion similarity may be based on various features of the lesion such as location, geometry (e.g., dimensions), tissue state, and so on. Lesion similarity may be determined using various similarity scoring techniques such as cosine similarity, Euclidean distance, Pearson Correlation Coefficient, L1 Norm, and so on. The PFA planning system then outputs the DP of the mapping. The lesion similarity criterion may be satisfied when a lesion similarity (score) exceeds a lesion similarity threshold. To verify the effectiveness of the lesion, the PFA planning system may run a lesion evaluation simulation based on the patient CC to determine if the lesion would be effective.

The PFA planning system may also output a 3D graphic of a heart that illustrates a lesion. Techniques for generating such a graphic are described in the '432 patent. For example, when a mapping is identified from the DP library, the PFA planning system may display a graphic based on the CC set of that mapping (or a patient CC set) that includes an indication of the lesion. The person may use the 3D graphic in evaluating whether to employ the DP of the mapping. The PFA planning system may also store as part of the mappings an indication of the lesion that has been developed so far at various times during a lesion development simulation such as at lesion evaluation intervals. In such a case, the PFA planning system may display a 3D graphic of the lesion as it develops over time. The PFA planning system may also provide a textual display of lesion characteristics, the DP that would develop the lesion, the CC set, the CG, and so on.

The PFA system may display a 3D graphic of a heart to illustrate lesion development. The 3D graphic may be based on a 3D mesh employed to simulate lesion development or employed to evaluate lesion effectiveness. The 3D graphic may include, for example, 16 sublayers spanning the thickness of the myocardium. When a 3D graphic is generated based on a 3D mesh, the PFA planning system adds an indication of the extent of the lesion to the sublayers. When different sublayers are selected for display by a user, the user may analyze the sublayers to assess the depth of the myocardial source. In addition, the SLR system may also display a 2D graphic representing a slice of the 3D graphic. Such a 2D graphic represents all the sublayers of the myocardium that may illustrate the depth of the lesion within the myocardium. The PFA planning system provides a user interface to allow selection of a sublayer or a slice that is to be displayed. A slice may be indicated by an azimuthal angle and a polar angle.

The PFA planning system may allow a user to rotate the 3D graphic of the heart through any orientation, that is, any spherical angle (e.g., azimuthal angle and polar angle.) By rotating the graphic, the user may better understand the lesion geometry. The graphic of the heart may be generated from a 3D image (e.g., CT scan) of the patient's heart. The PFA planning system may employ the Blender open-source system to generate, display, and rotate the graphic. (Blender Foundation, Blender, version 2.93, Blender, 2023. [Online]. Available: https://www.blender.org/.)

The PFA planning system may also identify a candidate path for the catheter during an ablation procedure. Techniques for identifying a candidate path are described in U.S. Pro. App. No. 63/550,020 titled "Cardiac Catheter Path Planning System" and filed on Feb. 5, 2024, which is hereby incorporated by reference. The candidate path may also be displayed on a 3D graphic of a heart.

Although the PFA planning system is described primarily in the context of simulating lesion development, the PFA planning system may identify a DP based on electronic health records (EHRs) of patients who have had successful PFA procedures. An EHR may include CC sets, a cardiogram collected prior to a procedure, a source location, the actual ablation location, the DP used in the procedure, a pre-procedure and post-procedure cardiac scan, and so on. The scans may include, for example, one or more of sestamibi, positron emission tomography (PET), echography, CT, voltage mapping, and magnetic resonance imaging (MRI) scans. As described in the '432 patent, the tissue state may be normal, borderzone, and scar that ranges from normal to no metabolic activity. The difference in tissue state from a pre-procedure scan to a post-procedure indicates the lesion characteristics. As described above, the PFA planning system may maintain mappings of CC sets to DPs and lesion characteristics derived from the EHRs. The PFA planning system may use the mappings based on EHRs in a manner analogous to how the mappings based on simulations are used.

The PFA planning system may output the DP (and target location) of a treatment plan to a PFA device for implementing the DP. When the catheter is at the target location, the ablation is performed based on the DP. The PFA device may also control movement of the catheter to the target location, for example, following a candidate path that is identified as described above. The PFA planning system may integrate with other systems employed during an ablation procedure using techniques described in PCT Pub. No. WO 2024/055046 titled "Integration of Electrophysiological Procedure System" and published on Mar. 14, 2024, which is hereby incorporated by reference.

After an ablation is performed, the PFA planning system may assess the effectiveness of the ablation. For example, a catheter may be employed to induce an arrhythmia by pacing an electrode. The PFA planning system may evaluate a cardiogram collected during pacing to determine whether the arrhythmia has been terminated or otherwise improved. If the arrhythmia is not improved, a mapping system may be employed to identifying the source location of the arrhythmia. For example, if the ablation was a PVI, the mapping system may identify a source location resulting from a gap in the ablation line of the PVI. The PFA planning may then be used to identify a DP for a target location that is the source location.

Various techniques may be employed to determine similarity (e.g., CC set or CG) such as a dot product, cosine similarity, Euclidean distance, Pearson Correlation Coefficient, L1 Norm, and so on. The similarity criterions may be based on a similarity (metric or score) exceeding a threshold similarity. To determine similarity, the most informative features of, for example, the CCs or the initial DPs, are identified. The features with higher variances may be selected. Other techniques for identifying informative features include correlation coefficients, mutual information, principal component analysis, and recursive feature elimination. The features selected depend on the feature that are available. For example, EHRs from different databases may have different sets of features. As another example, the sets of CCs may vary based on the legion development software employed to simulate lesion development. In such as case, informative features for one legion development software may be different from those for another legion development software even though they may be based on the same features.

The PFA planning system may employ various machine learning (ML) models to identify a DP for a patient. A first ML model may input a CC set and/or a CG and output a DP and/or a lesion characteristics (e.g., lesion geometry). A second ML model may input lesion characteristics and a CC set and/or a CG and output a DP. A third ML model may input a DP and a CC set and/or CG and output lesion characteristics. The training data for the ML models may be derived from a DP library based on the simulations or the EHRs.

An ML model may be any of a variety or combination of supervised, semi-supervised, self-supervised, unsupervised, or reinforcement learning ML models including a neural network such as fully connected, convolutional, recurrent, or autoencoder neural network, or restricted Boltzmann machine, a support vector machine, a Bayesian classifier, k-means clustering, decision tree, generative adversarial networks, transformer, and so on. When the ML model is a deep neural network, the model is trained using training data that includes features derived from data and labels corresponding to the data. For example, the data may be images or voltage-time series of ECGs and CC sets, with a feature being the image or the voltage-time series itself and a feature being a portion or all of a CC set, and the labels may be a DP or lesion characteristics. The training results in a set of weights for the activation functions of the layers of the deep neural network. The trained deep neural network can then be applied to new data to generate a label for that new data.

A neural network model has three major components: architecture, loss function, and search algorithm. The architecture defines the functional form relating the inputs to the outputs (in terms of network topology, unit connectivity, and activation functions). The search in weight space for a set of weights that minimizes the loss function is the training process. A neural network model may use a radial basis function (RBF) network and a standard or stochastic gradient descent as the search technique with backpropagation. The PFA planning system may employ a fully-connected NN with, for example, 10 hidden layers with 64 neurons each and employ a cross-entropy loss function.

A convolutional neural network (CNN) has multiple layers such as a convolutional layer, an ReLU layer, a pooling layer, a fully connected (FC) layer, and so on. Some more complex CNNs may have multiple convolutional layers, pooling layers, and FC layers. Each layer includes a neuron for each output of the layer. A neuron inputs outputs of prior layers (or original input) and applies an activation function to the inputs to generate an output.

The PFA planning system may employ a CNN to, for example, generate a segmentation of a CT scan to identify the chambers. A convolutional layer may include multiple filters (also referred to as kernels or activation functions). A filter inputs a convolutional window, for example, of an image, applies weights to each pixel of the convolutional window, and outputs value for that convolutional window. For example, if the static image is 256 by 256 pixels, the convolutional window may be 8 by 8 pixels. The filter may apply a different weight to each of the 64 pixels in a convolutional window to generate the value.

An activation function has a weight for each input and generates an output by combining the inputs based on the weights. The activation function may be a rectified linear unit (ReLU) that sums the values of each input times its weight to generate a weighted value and outputs max (0,weighted value) to ensure that the output is not negative. The weights of the activation functions are learned when training an ML model. The ReLU function of max (0,weighted value) may be represented as a separate ReLU layer with a neuron for each output of the prior layer that inputs that output and applies the ReLU function to generate a corresponding "rectified output."

A pooling layer may be used to reduce the size of the outputs of the prior layer by downsampling the outputs. For example, each neuron of a pooling layer may input 16 outputs of the prior layer and generate one output resulting in a 16-to-1 reduction in outputs.

An FC layer includes neurons that each input all the outputs of the prior layer and generates a weighted combination of those inputs. For example, if the penultimate layer generates 256 outputs and the FC layer inputs a neuron for each of three classifications (e.g., AF, VF, AFL), each neuron inputs the 256 outputs and applies weights to generate value for its classification.

One example of a CNN is a U-Net ML model. The U-Net ML model includes a contracting path and an expansive path. The contracting path includes a series of max pooling layers to reduce spatial information of the input image and increase feature information. The expansive path includes a series of upsampling layers to convert the feature information to the output image. The input and output of a U-Net represent an image such as an image of patient ECG as input and an image of a base region as output.

An unsupervised ML technique trains an ML model using unlabeled training data. An example ML technique is k-means clustering. Given feature vectors representing the training data, k-means clustering clusters the feature vectors into cluster of similar feature vectors. With k-means clustering, the number of clusters may be predefined. For example, the classification system may employ 100 clusters (k=100) to represent clusters of similar CC sets. Initially, an example training technique randomly places a feature vector (e.g., a CC set) in each cluster. The training then repeatedly calculates a mean feature vector of each cluster, selects a feature vector not in a cluster, identifies the cluster whose mean is most similar, adds the feature vector to that cluster, and moves the feature vectors already in the clusters to the cluster with the most similar mean. Similarity may be determined, for example, based on cosine similarity, Euclidean distance, Pearson Correlation Coefficient, L1 Norm, and so on. The training ends when all the feature vectors have been added to a cluster. Each cluster may be associated with a DP that is determined to be effective for the CC sets of that cluster. To identify a DP, a feature vector is generated based on the patient CC set, the cluster with a mean that is most similar to that feature vector is identified, and the DP is a suggested DP to inform treatment of the patient.

In some embodiments, a kNN model provides information relating to an entity. The training data for a kNN model may be training feature vectors (e.g., ECGs and CC set) and a label for each feature vector indicating information relating to an entity (e.g., DP) having the values of the features of that feature vector. A kNN model may be used without a training phase that is without learning weights or other parameters to represent the training data. In such a case, the patient feature vector is compared to the training feature vectors to identify a number (e.g., represented by the "k" in kNN) of similar training feature vectors. Once the number of similar training feature vectors are identified, the labels associated with the similar training feature vectors are analyzed to provide information for the entity. The labels of the training feature vectors that are more similar to an entity feature vector may be given a higher weight than those that are less similar. For example, if k is 10 and four training feature vectors are very similar and six are less similar, similarity weights of 0.9 may be assigned to the very similar training feature vectors and 0.2 to the less similar. If three of the four and one of the six have the same information, then the information for the entity is primarily based on that information even though most of the 10 have different information. Conceptually, training feature vectors that are very similar are closer to the entity feature vector in a multi-dimensional space of features and a similarity weight is based on distance between the feature vectors. Various techniques may be employed to calculate a similarity metric indicating similarity between a candidate feature vector and a training feature vector such as a dot product cosine similarity, Euclidean distance, Pearson Correlation Coefficient, L1 Norm, and so on.

If the number of training feature vectors is large, various techniques may be employed to effectively "compress" the training data during a training phase. For example, a clustering technique may be employed to identify clusters of training feature vectors that are similar and have the same label. A training feature vector may be generated for each cluster (e.g., one from the cluster or one based on mean values for the features) as a cluster feature vector and assign a cluster weight to it based on number of training feature vectors in the cluster.

The ML models that input a cardiogram input a feature vector of one or more features derived from the cardiogram. The features may include an image of cardiogram, a voltage-time series specifying voltages and time increments of the cardiogram, images and voltage-time series of portions of the cardiogram (e.g., QRS complex), length in seconds of various intervals (e.g., R-R interval, QRS complex, T wave, T-Q interval, and Q-R interval), QRS integral, maximum, minimum, mean, and variance of voltages of portions of the cardiogram, a maximal vector of QRS loop and angle of the vector derived from VCG, location of a peak (Q peak) or zero crossing relative to a maximum peak (T peak) in an interval, and so on. The features used by an ML model may be manually or automatically selected. An assessment of which features may be useful in providing an accurate output for an ML model are referred to as informative feature. The assessment of which features are informative may be based on various feature selection techniques such as a predictive power score, a lasso regression, a mutual information analysis, and so on.

The features may also be latent vectors generated using an ML model such as an autoencoder. For example, an autoencoder may be trained using ECG images. In such a case, when an ECG image is input into the trained autoencoder, the latent vector that is generated is a feature vector that represents the ECG image. That feature vector can be input into another trained ML model such as a neural network or support vector machine to generate an output. When training the other ML model, for example, to classify an ECG as representing an atrial fibrillation or a ventricular fibrillation, the training ECG images are input to the autoencoder to generate training feature vectors that are labeled as being atrial fibrillation or ventricular fibrillation. The other ML model is then trained using the labeled feature vectors. The autoencoder may be trained using the training ECG images or may have been previously trained using a collection of ECG images. Rather pre-training an autoencoder, only the portion of the autoencoder that generates the latent vector may be trained in parallel with the other ML model using a combined loss function. In such a case, no autoencoding is performed. Rather the latent vector represents features of an ECG image that are particularly relevant to generating the output of the other ML model. Such an ML architecture may be used, for example, when the other ML model (e.g., transformer) is not designed to process ECG images directly.

The PFA planning system may employ transformer as an ML model to, for example, to generate a DP given a CC set. Transformer machine learning was introduced as an alternative to a recurrent neural network that is both more effective and more parallelizable. (See, Vaswani, A., Shazeer, N., Parmar, N., Uszkoreit, J., Jones, L., Gomez, A. N., Kaiser, Ł. and Polosukhin, I., 2017. Attention is all you need. *Advances in neural information processing systems,* 30, which is hereby incorporated by reference.) Transformer machine learning was originally described in the context of natural language processing (NLP) but has been adapted to other applications such as image processing to augment or replace a CNN.

A transformer includes an encoder whose output is input to a decoder. The encoder includes an input embedding layer followed by one or more encoder attention layers. The input embedding layer generates an embedding of the inputs.

The first encoder attention layer inputs the embeddings and the other encoder attention layers input the output from the prior encoder attention layer. An encoder attention layer includes a multi-head attention mechanism followed by a normalization sublayer whose output is input to a feedforward neural network followed by a normalization sublayer. A multi-head attention mechanism includes multiple self-attention mechanisms that each inputs the encodings of the previous layer and weighs the relevance encodings to other encodings. For example, the relevance may be determined by the following attention function:

$$\text{Attention}(Q, K, V) = \text{softmax}\left(\frac{QK^T}{\sqrt{d_k}}\right)V$$

where Q represents a query, K represents a key, V represents a value, and $d_k$ represents the dimensionality of K. This attention function is referred to as scaled dot-product attention. In Vaswani, the query, key, and value of an encoder multi-head attention mechanism is set to the input of the encoder attention layer. The multi-head attention mechanism determines the multi-head attention as represented by the following:

$$\text{MultiHead}(Q, K, V) = \text{concat}(\text{head}_1, \ldots, \text{head}_8)W^o$$

$$\text{head}_1 = \text{Attention}\left(QW_i^Q, KW_i^K, VW_i^V\right)$$

where W represents weights that are learned during training. The weights for the feedforward networks are also learned during training. The weights may be initialized to random values. A normalization layer normalizes its input to a vector having a dimension as expected by the next layer or sub-layer.

The decoder includes an output embedding layer, decoder attention layers, a linear layer, and a softmax layer. The output embedding layer inputs the output of the decoder shifted right. Each decoder attention layer inputs the output of the prior decoder attention layer (or the output embedding layer) and the output of the encoder. The embedding layer is input to the decoder attention layer, the output of the decoder attention layer is input the linear layer, and the output of the linear layer is input to the softmax layer which outputs probabilities. A decoder attention layer includes a decoder masked multi-head attention mechanism followed by a normalization sublayer, a decoder multi-head attention mechanism followed by a normalization sublayer, and a feedforward neural network followed by a normalization sublayer. The decoder masked multi-head attention mechanism masks the input so that predictions for a position are only based on outputs for prior positions. A decoder multi-head attention mechanism inputs the normalized output of the decoder masked multi-head attention mechanism as a query and the output of the encoder as a key and a value. The feedforward neural network inputs the normalized output of the decoder multi-head attention mechanism. The normalized output of the feedforward neural network is the output of that multi-head attention layer. The weights of the linear layer are also learned during training.

FIG. 1 is a flow diagram that illustrates the processing of an evaluate CC/DP component in some embodiments. The evaluate CC/DP component 100 inputs a CC set and a DP and determines whether a lesion developed based on the DP would be effective in treating a patient with a heart with CCs similar to those of the CC set. In block 101, the component runs a lesion development simulation to simulate the development of a lesion based on the input CC set and DP. In block 102, the function runs a lesion evaluation simulation to evaluate the effectiveness of the lesion. In decision block 103, if the lesion evaluation simulation indicates that the lesion would be effective at treating the patient, then the component continues at block 104, else the component completes. In block 104, the component stores a mapping of the CC set to the DP in the DP library and then completes. The processing described above may also be employed to evaluate a DP given a CC set derived from a patient. Such a CC set is considered to be patient-specific or a digital twin of the patient. Multiple DPs may be evaluated to allow a physician to select from multiple DPs.

Figure 2:
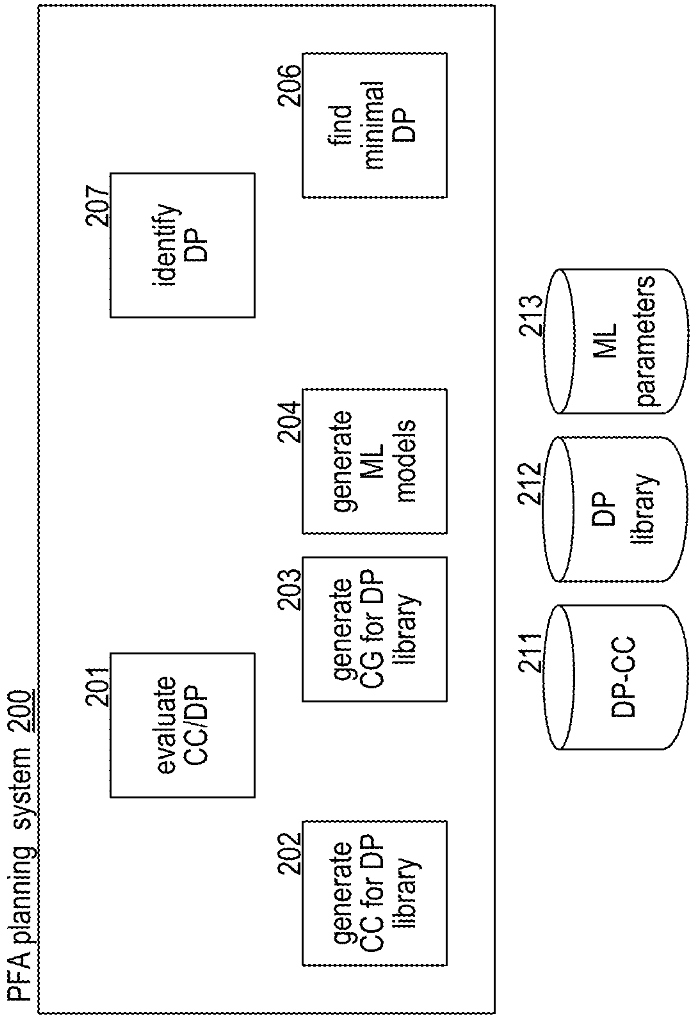
FIG. 2 is a block diagram that illustrates components and data stores of the PFA planning system in some embodiments.

FIG. 2 is a block diagram that illustrates components and data stores of the PFA planning system in some embodiments. The PFA planning system 200 includes an evaluate CC/DP component 201, a generate CC for DP library component 202, a generate CG for DP library component 203, a generate ML models component 204, a find minimal DP component 206, and an identify DP component 207. The PFA planning system also includes a DP-CC data store 211, a DP library data store 212, and an ML model parameters data store 213. The evaluate CC/DP component evaluates the effectiveness of a DP on a heart with CCs of a CC set. The generate CC for DP library component generates and stores in the DP library mappings of CC sets to effective DPs. The generate CGs for DP library component stores in the DP library mappings of CGs to effective DPs. The generate ML models component trains various ML models.

A CC-CG/DP ML model maps CCs and/or CGs to DPs. A lesion-CC-CG/DP ML model maps lesions and CCs and/or CGs to DPs. A lesion ML model maps DPs and CCs and/or CGs to lesions. The DP-CC data store contains specifications of DPs and specifications of CC sets. The DP library data store contains mappings of CCs and/or CGs to DPs and/or lesions. The ML parameters data store contains parameters (e.g., weights and biases) of a trained ML models.

The computing systems (e.g., network nodes or collections of network nodes) on which the PFA planning system and the other described systems may be implemented may include a central processing unit, graphic processing units, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, distributed systems, cloud-based computing systems, client computing systems that interact with cloud-based computing system, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the PFA planning system and the other described systems. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extension (SGX)) for generating and securely storing keys and for encrypting and decrypting data using the keys and for securely executing all or some of the computer-executable instructions of the PFA planning system. Some of the data sent by and received by the PFA planning system may be encrypted, for example, to preserve patient privacy (e.g., to comply with government regulations such the European General Data Protection Regulation (GDPR) or the Health Insurance Portability and Accountability Act (HIPAA) of the United States). The PFA planning system may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each executes computer-executable instructions of the PFA planning system. A client-side computing system may send data to and receive data from one or more servers of the cloud-based computing systems of one or more cloud data centers. For example, a client-side computing system may send a request to a cloud-based computing system to perform tasks such as run a patient-specific simulation of electrical activity of a heart or train a patient-specific ML model. A cloud-based computing system may respond to the request by sending to the client-side computing system data derived from performing the task such as a source location of an arrhythmia. The servers may perform computationally expensive tasks in advance of processing by a client-side computing system such as training an ML model or in response to data received from a client-side computing system. A client-side computing system may provide a user experience (e.g., user interface) to a user of the PFA planning system. The user experience may originate from a client computing device or a server computing device. For example, a client computing device may generate a patient-specific graphic of a heart and display the graphic. Alternatively, a cloud-based computing system may generate the graphic (e.g., in a Hyper-Text Markup Language (HTML) format or an extensible Markup Language (XML) format) and provide it to the client-side computing system for display. A client-side computing system may also send data to and receive data from various medical devices such as an ECG monitor, an ablation therapy device, an ablation planning device, and so on. The data received from the medical devices may include an ECG, actual ablation characteristics (e.g., ablation location and ablation pattern), and so on. The data sent to a medical device may be, for example, in a Digital Imaging and Communications in Medicine (DICOM) format. A client-side computing device may also send data to and receive data from medical computing systems that store patient medical history data, descriptions of medical devices (e.g., type, manufacturer, and model number) of a medical facility, that store, medical facility device descriptions, that store results of procedures, and so on. The term cloud-based computing system may encompass computing systems of a public cloud data center provided by a cloud provider (e.g., Azure provided by Microsoft Corporation) or computing systems of a private server farm (e.g., operated by the provider of the PFA planning system).

The PFA planning system and the other described systems may be described in the general context of computer-executable instructions, such as program modules and components, executed by one or more computers, processors, or other devices. Generally, program modules or components include routines, programs, objects, data structures, and so on that perform tasks or implement data types of the PFA planning system and the other described systems. Typically, the functionality of the program modules may be combined or distributed as desired in various examples. Aspects of the PFA planning system and the other described systems may be implemented in hardware using, for example, an application-specific integrated circuit (ASIC) or a field programmable gate array (FPGA).

Figure 3:
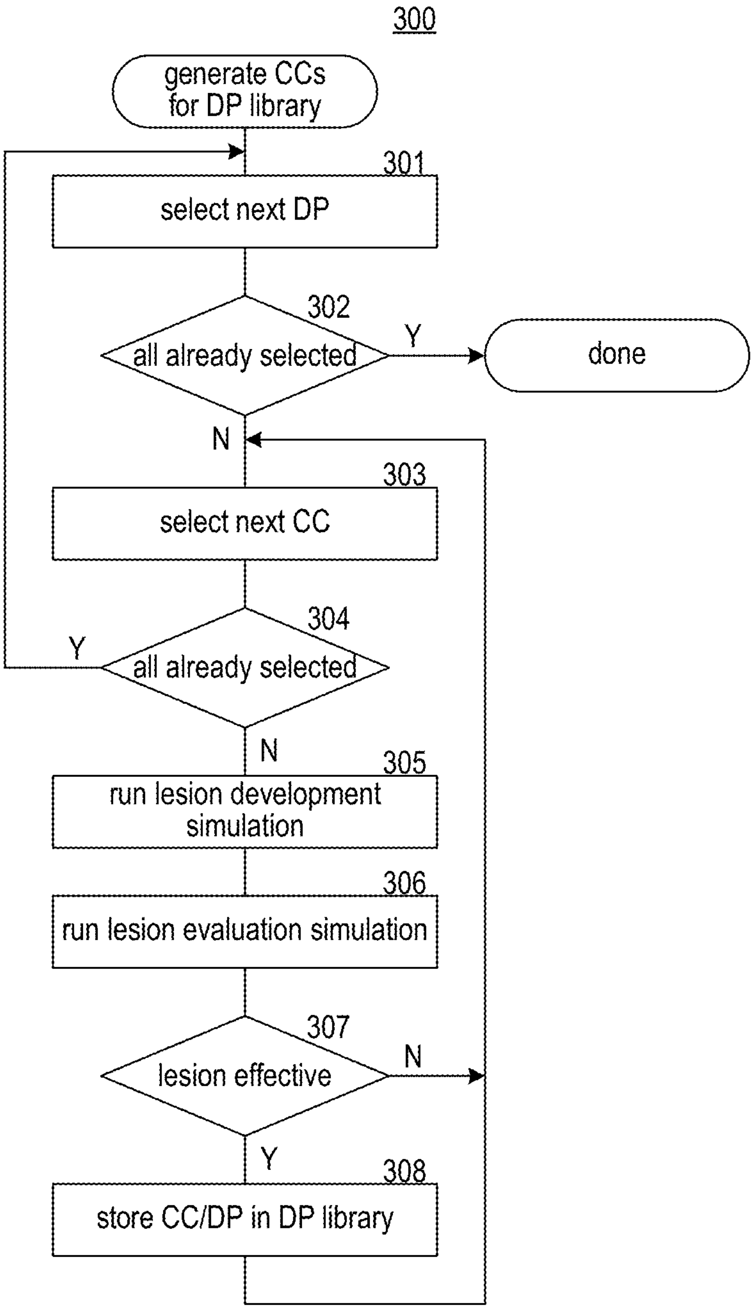
FIG. 3 is a flow diagram that illustrates the processing of a generate CC/DP library for CC sets component in some embodiments.

FIG. 3 is a flow diagram that illustrates the processing of a generate CCs for DP library component in some embodiments. The generate CCs for DP library component 300 runs lesion development simulations and lesion evaluation simulations and adds mappings of CC sets to DPs for effective lesions in the DP library. In block 301, the component selects the next DP of the DP-CC data store. In decision block 302, if all the DPs have already been selected, then the component completes, else the component continues at block 303. In block 303, the component selects the next CC set of the DP-CC data store. In decision block 304, if all the CC sets have already been selected, then the component loops to block 301 to select the next DP, else the component continues at block 305. In block 305, the component runs a lesion development simulation to develop a lesion based on the selected DP and the selected CC set. In block 306, the component runs a lesion evaluation simulation based on the lesion and the selected CC set. In decision block 307, if the lesion evaluation simulation indicates that the lesion satisfies a lesion effectiveness criterion, then the component continues at block 308, else the component loops to block 303 to select the next CC set. In block 308, the component stores a mapping of the CC set to the DP in the DP library and then loops to block 303 to select the next CC set. The component may include in the mapping an indication of the lesion. In some embodiments, the component may employ a simulation bootstrapping technique to speed up the running of the simulations. For example, a lesion development simulation may be initialized based on a previously run lesion development simulation whose DP and CC set are similar to the selected DP in the selected CC set based on a DP/CC similarity criterion. A lesion evaluation simulation may be initialized based on the lesion evaluation simulation that was run for the previously run lesion development simulation. Techniques for bootstrapping a simulation are described in the '754 patent.

Figure 4:
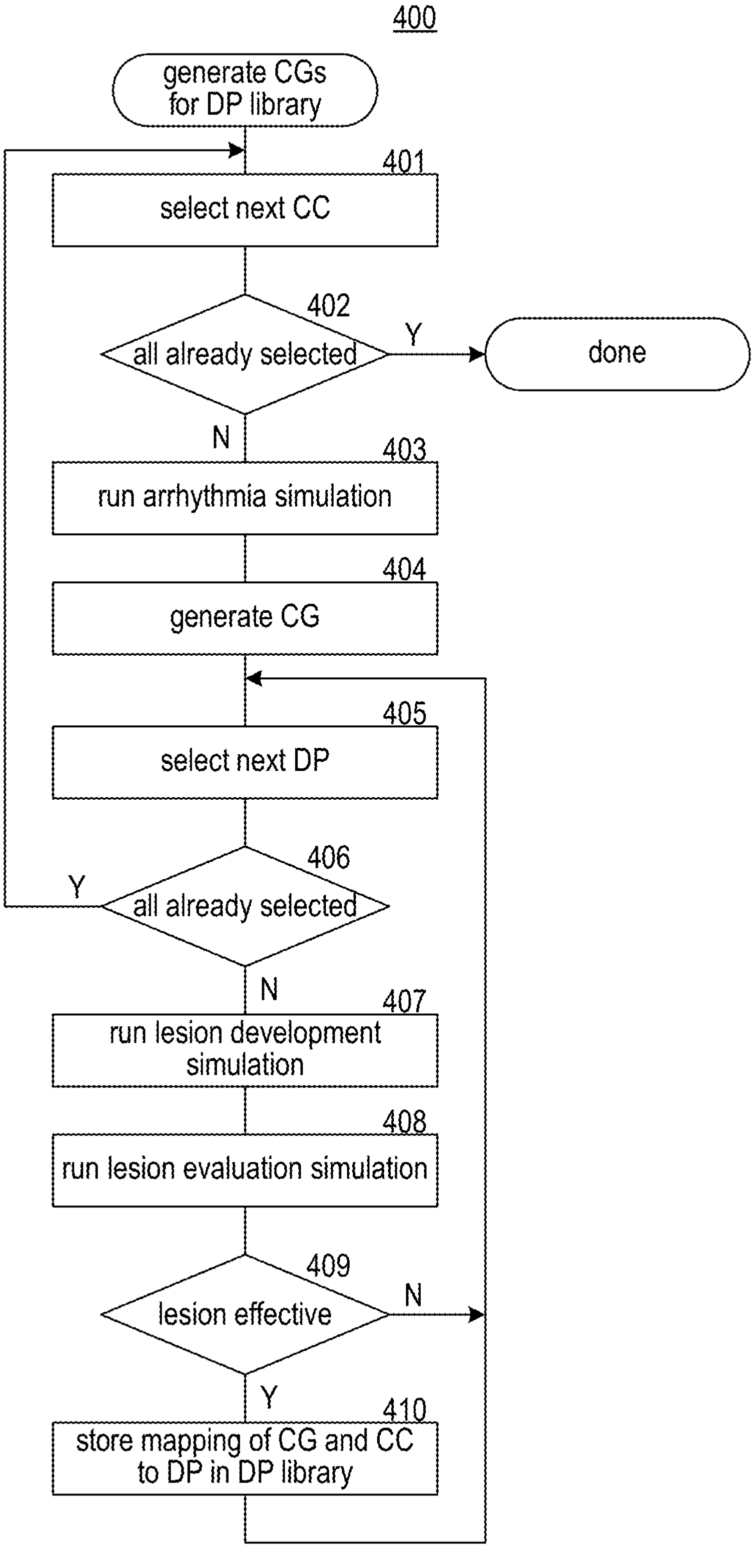
FIG. 4 is a flow diagram that illustrates the processing of a generate CGs for DP library component in some embodiments.

FIG. 4 is a flow diagram that illustrates the processing of a generate CGs for DP library component in some embodiments. The generate CGs for DP library component 400 runs arrhythmia simulations, lesion development simulations, and lesion evaluation simulations and adds mappings of CGs and CC sets to DPs for effective lesions in the DP library. In block 401, the component selects the next CC set of the DP-CC data store. In decision block 402, if all the CC sets have already been selected, then the component completes, else the component continues at block 403. In block 403, the component runs an arrhythmia simulation based on the selected CC set to determine whether an arrhythmia develops. If an arrhythmia does not develop, then the component continues at block 401 (not shown) to select the next CC set. In block 404, the component generates a CG based on the simulated electrical activity of the arrhythmia simulation. In some embodiments, the arrhythmia simulations and the generation of the CG may have been previously performed for each CC set. Techniques for generating body surface potential measurements (e.g., electrocardiograms) from simulations of cardiac electrical activity is described in Yu, A. and Peng, H., 2008. Studies on the ECG forward problem. Computers & Electrical Engineering, 34(2), pp. 92-98, which is hereby incorporated by reference. In block 405, the component selects the next DP of the DP-CC data store. In decision block 406, if all the DPs have already been selected, then the component loops to block 401 to select the next CC set, else the component continues at block 407. In block 407, the component generates a lesion by running a lesion development simulation based on the selected DP and the selected CC set. In block 408, the component runs a lesion evaluation simulation based on the lesion and the selected CC set. In decision block 409, if the lesion evaluation simulation indicates that the lesion satisfies a lesion effectiveness criterion, then component continues at block 410, else the component loops to block 405 to select the next DP. In block 410, the component stores a mapping of the CC and CG to the DP in the DP library and loops to block 405 to select the next DP. The component may also include in the mapping an indication of the lesion. In some embodiments, the component may employ a simulation bootstrapping technique to speed up the running of the arrhythmia simulation as described in the '754 patent and the running of the lesion development simulation and the lesion evaluation simulation as described above in reference to FIG. 3.

Figure 5:
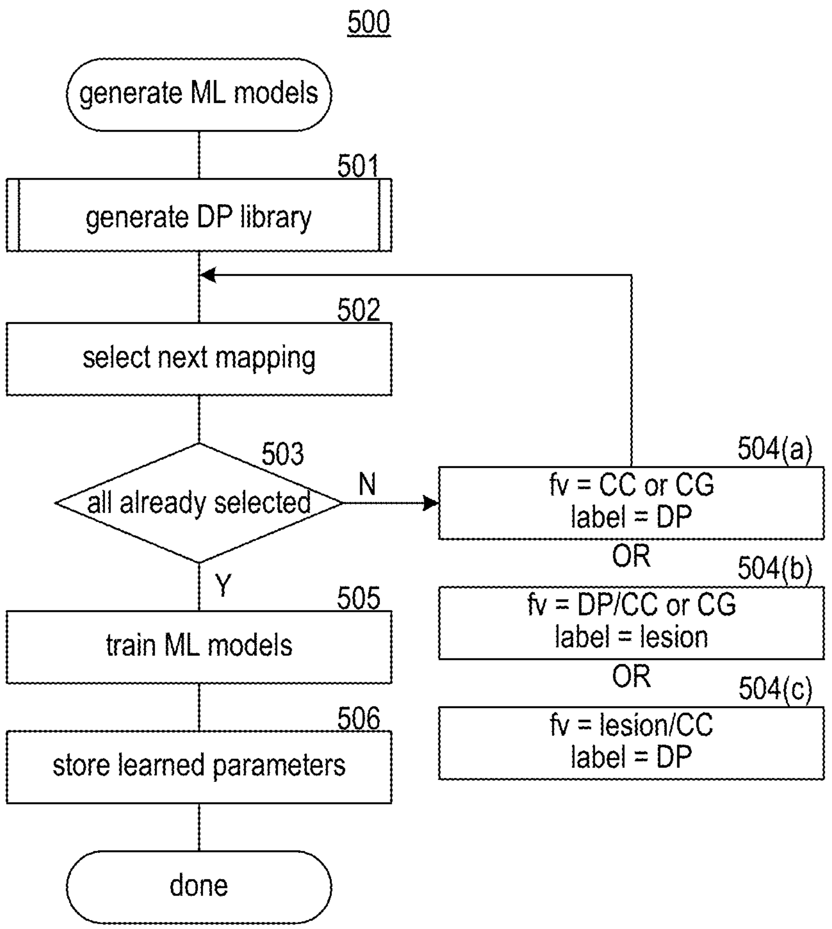
FIG. 5 is a flow diagram that illustrates the processing of a generate ML models component in some embodiments.

FIG. 5 is a flow diagram that illustrates the processing of a generate ML models component in some embodiments. The generate ML models component 500 generates a DP library, generates training data, and trains the ML models. FIG. 5 illustrates the training of an ML model that inputs a CC set and/or CG and outputs a DP, an ML model that inputs a DP and a CC set and/or CG and outputs a lesion, and an ML model that inputs a lesion and a CC set and/or a CG and outputs a DP. In block 501, the component invokes a generate DP library component to generate a DP library that maps CC sets and/or CGs to DPs or lesions. In block 502, the component selects the next mapping of the DP library. In block 503, if all the mappings have already been selected, then the component continues at block 505, else the component continues at block 504. Blocks 504 (*a*), 504 (*b*), and 504 (*c*) illustrate the generating of a training data set of the training data for different ML models. In block 504 (*a*), generates a feature vector that includes a CC set and/or a CG that is labeled with a DP. In block 504 (*b*), the component generates a feature vector that includes a DP and a CC set and/or CG that is labeled with a lesion. In block 504 (*c*), the component generates a feature vector that includes a lesion and a CC set and/or CG that is labeled with a DP. The component then loops to block 502 to select the next mapping. In block 505, the component trains the ML models with the training data. In block 506, the component stores the learned parameters of the ML models in the DP ML parameters data store and then completes. In some embodiments, the component may employ transference of parameters (e.g., weights and biases) in training an ML model as described in the '754 patent.

Figure 6:
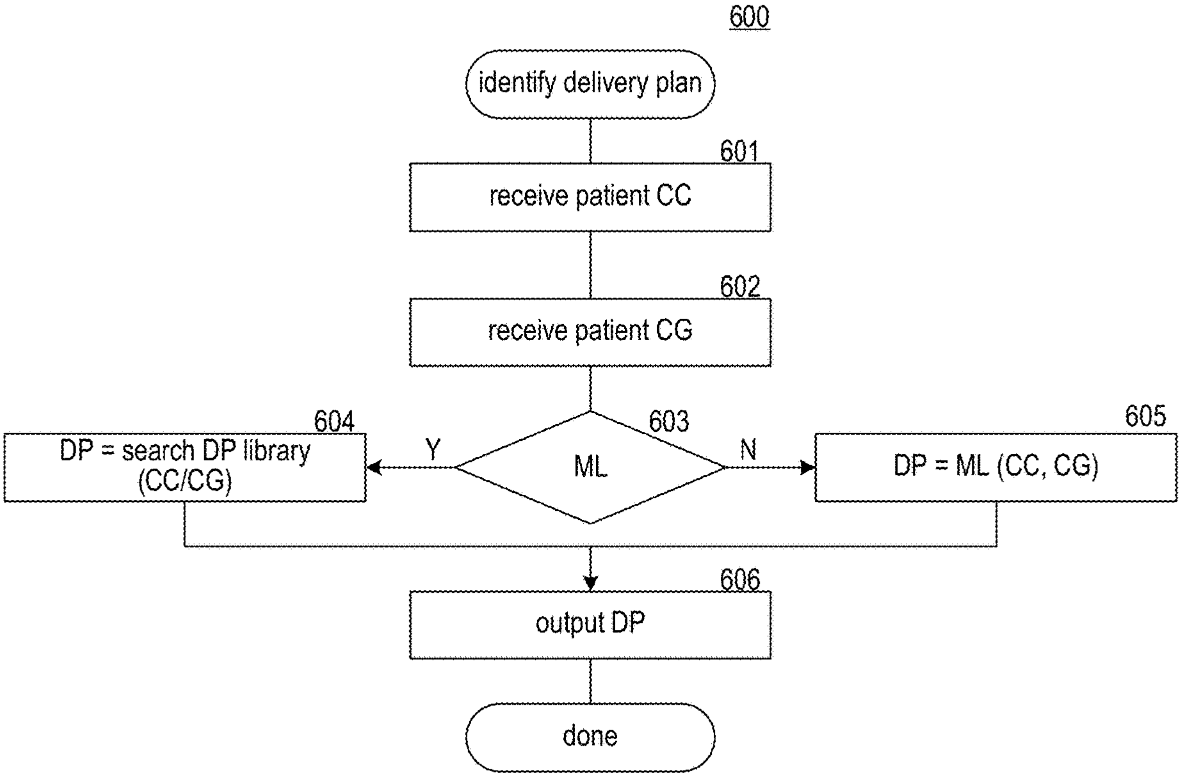
FIG. 6 is a flow diagram that illustrates the processing of an identify delivery plan component in some embodiments.

FIG. 6 is a flow diagram that illustrates the processing of an identify delivery plan component in some embodiments. The identify delivery plan component 600 is invoked to identify a delivery plan for patient based a CC set and a CG. The identification of a delivery plan may also be based on a CC set only, a CG only, and a lesion and a CC set and/or a CG. The component supports identifying the DP based on searching the DP library or based on an ML model. In block 601, the component receives the patient CC set for a patient. In block 602, the component receives a patient CG for the patient. In decision block 603, if an ML model is to be used for identifying the DP, then the component continues at block 605, else the component continues at block 604. In block 604, the component searches the DP library to find a mapping of the CC set and the CG (based on a CC similarity criterion and a CG similarity criterion) to a DP and retrieves the DP. In block 605, the component applies the ML model to a feature vector that includes the CC set and the CG which outputs a DP. In block 606, the component outputs the DP and completes.

Figure 7:
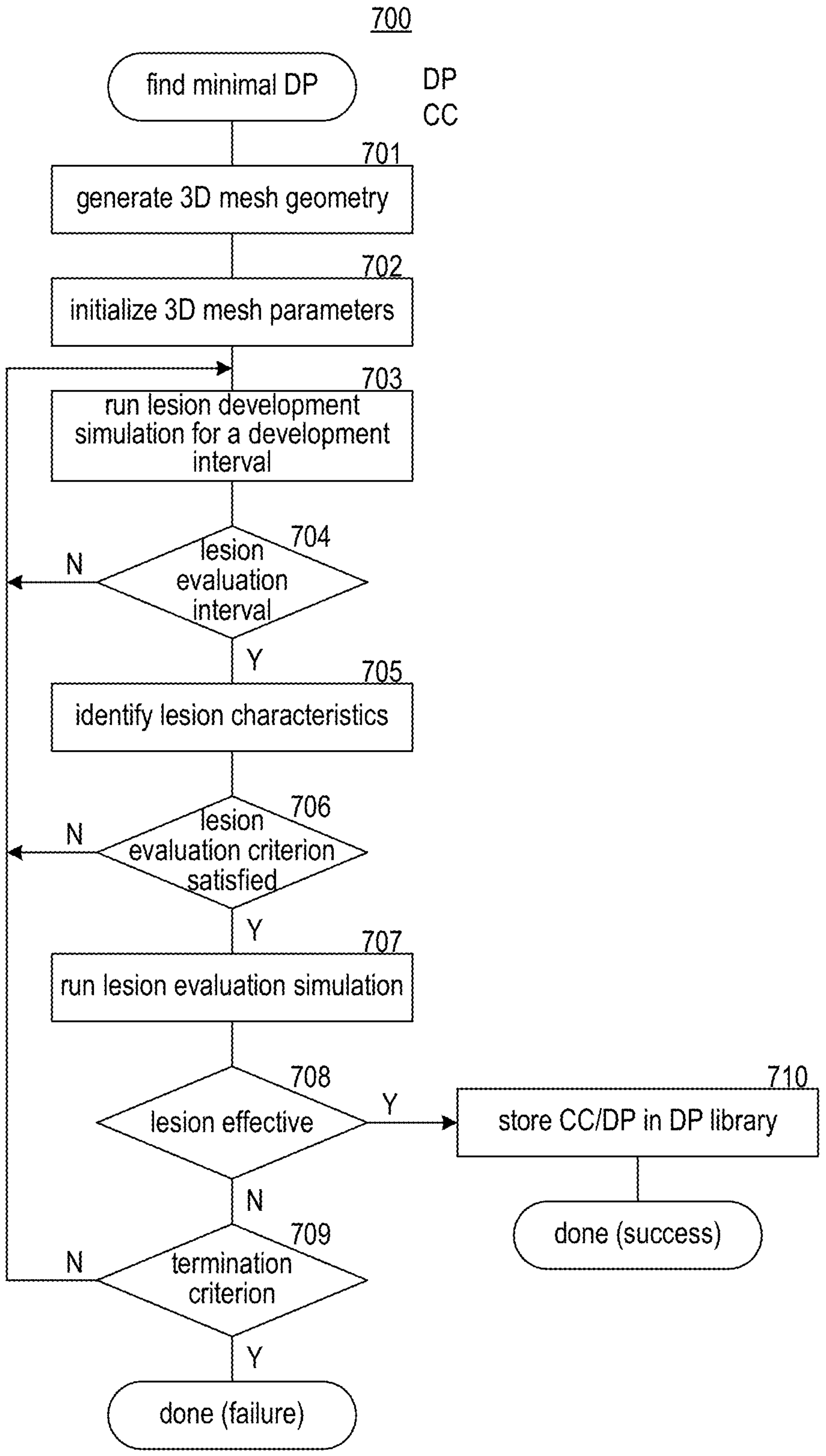
FIG. 7 is a flow diagram that illustrates the processing of a find minimal DP component in some embodiments.

FIG. 7 is a flow diagram that illustrates the processing of a find minimal DP component in some embodiments. The find minimal DP component 700 identifies the minimum initial portion of a DP that generates a lesion that is determined to be effective. When treating a patient, an ablation may be based on that minimum initial portion. In block 701, the component generates a 3D mesh based on the geometry of a CC set. In block 702, the component initializes the parameters of the 3D mesh. In blocks 703-709, the component incrementally runs a lesion development simulation and evaluates effectiveness of the lesion at various simulation intervals. In block 703, the component runs a lesion development simulation for a development interval. In decision block 704, if the lesion development interval corresponds to a lesion evaluation interval, then the component continues at block 705, else the component loops to block 703 to run the lesion development simulation for the next lesion development interval. A lesion evaluation interval may be based on a certain number of lesion development intervals such as 10 or 20. In block 705, the component identifies lesion characteristics. In decision block 706, if a lesion evaluation criterion is satisfied, then the component loops to block 703 to run a lesion development simulation for the next lesion development interval. The lesion evaluation criterion may be based on various features derived from the lesion such as lesion volume, maximum lesion width, tissue characteristics (e.g., conductivity and permittivity), and so on. In block 707, the component runs a lesion evaluation simulation which may be a continuation of the last lesion evaluation simulation. In decision block 708, if the lesion is determined to be effective, then the component continues at block 710, else the component continues at block 709. In decision block 709, if the lesion termination criterion is satisfied, then the component completes, else the component loops to block 703 to run the lesion development simulation for the next lesion development interval. The termination criterion may be based on various factors such as lesion volume, closeness to a protected structure (e.g., phrenic nerve), number of lesion development intervals, and so on. In block 710, the component stores a mapping of the CC to the initial portion of the DP and then completes.

Although the PFA planning system is described above in the context of using simulations to generate the DP library, data of the DP library may be based on EHRs of patients who had ablation procedures. The CC sets and the lesion characteristics may be derived from post-procedure images (e.g., MRI or CT) of a patient's heart. For a mapping, some of the data can be derived from an EHR and the rest of the data may be simulated. For example, a CC set and CG may be derived from an EHR, and a lesion may be simulated based on a DP.

All documents incorporated by reference are incorporated in their entirety for the full extent of their disclosures. In the event of inconsistencies between the language in this document and any incorporated-by-reference document, the language in the incorporated-by-reference document should be considered supplementary to that of this document and the language in this document controls.

The following paragraphs describe various aspects of the PFA planning system. An implementation of the PFA planning system may employ any combination or sub-combination of the aspects and may employ additional aspects. The processing of the aspects may be performed by one or more computing systems with one or more processors that execute computer-executable instructions that implement the aspects and that are stored on one or more computer-readable storage mediums.

In some aspects, the techniques described herein relate to a method performed by one or more computing systems for determining effectiveness of a delivery plan for an ablation for treating an arrhythmia, the method including: running a lesion development simulation based on cardiac characteristics and a treatment plan that specifies a delivery plan and a target location to generate a simulated lesion having lesion characteristics; initializing a three-dimensional (3D) mesh representing a heart based on cardiac characteristics, vertices of the 3D mesh associated with cardiac tissue characteristics, one or more vertices associated with cardiac tissue characteristics representing an arrhythmia source; adjusting the cardiac tissue characteristics of vertices of the 3D mesh to reflect the effect of an ablation resulting in formation of the simulated lesion; and running a lesion evaluation simulation based on the 3D mesh with the adjusted cardiac tissue characteristics to determine whether the simulated lesion would be effective at treating the arrhythmia. In some aspects, the techniques described herein relate to a method wherein the delivery plan specifies a delivery plan duration and an electrode activation plan, the electrode activation plan specifying voltage and a voltage duration for each electrode of an ablation device. In some aspects, the techniques described herein relate to a method wherein the cardiac characteristics include electrical conductivity and the lesion development simulation is based on an electric field generated by voltages and voltage durations of the electrode activation plan. In some aspects, the techniques described herein relate to a method wherein the lesion development simulation simulates electroporation of cardiac tissue. In some aspects, the techniques described herein relate to a method wherein the lesion development simulation simulates the effect of the electric field on transmembrane potential of cardiac tissue. In some aspects, the techniques described herein relate to a method wherein the transmembrane potential is based on cardiac tissue characteristics that include conductivity and permittivity. In some aspects, the techniques described herein relate to a method wherein the lesion development simulation simulates the effect of heat on cardiac tissue and blood. In some aspects, the techniques described herein relate to a method wherein the lesion development simulation simulates the effect of electrode pressure on the heart wall and electrode angle relative to the heart wall. In some aspects, the techniques described herein relate to a method wherein the 3D mesh is based on the geometry of a patient heart of a patient and the cardiac tissue characteristics are derived from the patient heart. In some aspects, the techniques described herein relate to a method further including prior to adjusting the cardiac characteristics, running an arrhythmia simulation of electrical activity of the heart represented by the 3D mesh based on the cardiac tissue characteristics until the electrical activity is consistent with an arrhythmia. In some aspects, the techniques described herein relate to a method wherein running of the lesion development simulation simulates a pulsed field ablation. In some aspects, the techniques described herein relate to a method wherein running of the lesion development simulation simulates a radiofrequency ablation. In some aspects, the techniques described herein relate to a method further including for each of a plurality of sets of cardiac characteristics, performing the initializing of a 3D mesh and for each of a plurality of treatment plans, performing the running of a lesion development simulation based on that treatment plan, the adjusting of cardiac tissue characteristics, and the running a lesion evaluation simulation. In some aspects, the techniques described herein relate to a method further including training a machine learning model using training data that includes for each combination of a set cardiac characteristics and treatment plans, generating a training data set that includes at least one feature derived from those cardiac characteristics, and one or more labels indicating that treatment plan and effectiveness of the simulated lesion developed based on that treatment plan. In some aspects, the techniques described herein relate to a method further including applying the trained machine learning model to at least one feature derived from cardiac characteristics of a patient to generate an indication of a treatment plan that may be effective at treating the patient. In some aspects, the techniques described herein relate to a method further including for a patient with patient cardiac characteristics that are similar to the cardiac characteristics, selecting a treatment plan based on effectiveness of the simulated lesion generated based on that treatment plan. In some aspects, the techniques described herein relate to a method further including when the effectiveness satisfies a lesion effectiveness criterion, providing the delivery plan and the target location to an ablation device that controls the performing of an ablation on a patient based on the delivery plan and the target location. In some aspects, the techniques described herein relate to a method further including when effectiveness satisfies a lesion effectiveness criterion, controlling the performing of an ablation on a patient based on the treatment plan. In some aspects, the techniques described herein relate to a method wherein the controlling including setting configuration parameters of an ablation device.

In some aspects, the techniques described herein relate to a method performed by one or more computing systems for assessing effectiveness of a delivery plan for an ablation, the method including: initializing a three-dimensional (3D) mesh representing a heart, each vertex of the 3D mesh associated with cardiac tissue characteristics, one or more vertices associated with cardiac tissue characteristics representing a source location of an arrhythmia; accessing the delivery plan for the ablation, the delivery plan specifying an electrode activation plan that specifies a voltage and a voltage duration for each electrode of an ablation device; and for each of a plurality of lesion development intervals, running a lesion development simulation for that lesion development interval based on the delivery plan to adjust cardiac tissue characteristics to reflect development of a simulated lesion during that lesion development interval; and when a lesion development interval corresponds to a lesion evaluation interval, running a lesion evaluation simulation based on the 3D mesh with the adjusted cardiac tissue characteristics the simulated lesion to determine whether the simulated lesion would be effective at treating the arrhythmia. In some aspects, the techniques described herein relate to a method wherein the lesion evaluation simulation simulates electrical activity of the heart with the adjusted cardiac tissue characteristics to determine whether an arrhythmia develops. In some aspects, the techniques described herein relate to a method wherein the electrode activation plan is part of a treatment plan that further specifies at least one or more of an ablation technology, a catheter type, an electrode configuration, a waveform of electrical pulses, an orientation of a catheter, a distance from or depth within the heart wall, and a contact force.

In some aspects, the techniques described herein relate to one or more computing systems for generating delivery plans, the one or more computing systems including: one or more computer-readable storage mediums that store computer-executable instructions for controlling the one or more computing systems to, for one or more cardiac characteristic sets: initialize a three-dimensional (3D) mesh representing a heart based on that cardiac characteristic set, vertices of the 3D mesh associated with cardiac tissue characteristics of the cardiac characteristics set, one or more vertices associated with cardiac tissue characteristics representing an arrhythmia source; and for one or more delivery plans, run a lesion development simulation to simulate the effect of that delivery plan on cardiac tissue, the effect including formation of a simulated lesion having lesion characteristics; adjust the cardiac tissue characteristics of vertices of the 3D mesh to reflect the lesion characteristics; run a lesion evaluation simulation based on the 3D mesh with the adjusted cardiac tissue characteristics to determine effectiveness of the simulated lesion; and based on a lesion evaluation simulation indicating that the delivery plan would satisfy a lesion effectiveness criterion, associate the delivery plan with the cardiac characteristic set; and one or more processors for controlling the one or more computing systems to execute one or more of the computer-executable instructions. In some aspects, the techniques described herein relate to one or more computing systems the instructions control the one or more computing systems to: access patient cardiac characteristic set of a patient; identify a cardiac characteristic set based on that cardiac characteristic set and the patient cardiac characteristics satisfying a cardiac characteristics similarity criterion; and output an indication of the delivery plan associated with the identified cardiac characteristic set. In some aspects, the techniques described herein relate to one or more computing systems wherein the instructions further control the one or more computing systems to, after initializing the 3D mesh, run an arrhythmia simulation of electrical activity of the heart represented by the 3D mesh based on the cardiac tissue characteristics until the electrical activity is consistent with an arrhythmia. In some aspects, the techniques described herein relate to one or more computing systems wherein the instructions further control the one or more computing systems to: generate a simulated cardiogram based on the simulated electrical activity of the arrhythmia simulation; and associating the simulated cardiogram with the delivery plan. In some aspects, the techniques described herein relate to one or more computing systems wherein the instructions further control the one or more computing systems to: access a patient cardiogram; identify a simulated cardiogram based on the patient cardiogram and the simulated cardiogram satisfying a cardiogram similarity criterion; and output an indication of the delivery plan associated with the identified simulated cardiogram. In some aspects, the techniques described herein relate to one or more computing systems wherein the instructions further control the one or more computing systems to train a machine learning model with training data that includes simulated cardiograms labeled with the associated delivery plans. In some aspects, the techniques described herein relate to one or more computing systems wherein the instructions further control the one or more computing systems to train a machine learning model with training data that includes cardiac characteristics labeled with the associated delivery plans.

In some aspects, the techniques described herein relate to a method performed by one or more computing systems for evaluating effectiveness of a delivery plan for an ablation in treating an arrhythmia, the method including: running a lesion development simulation based on the delivery plan and a cardiac characteristics set representing the arrhythmia to generate a simulated lesion; and running a lesion evaluation simulation with the cardiac characteristics set adjusted based on the simulated lesion to determine whether the simulated lesion would be effective in treating the arrhythmia. In some aspects, the techniques described herein relate to a method further including prior to running the lesion development simulation, running an arrhythmia simulation based on the cardiac characteristics set and an indication of a source of the arrhythmia to determine whether an arrhythmia develops. In some aspects, the techniques described herein relate to a method further including: for each of a plurality of combinations of cardiac characteristics sets and delivery plans, running a lesion development simulation and a lesion evaluation simulation; and training a machine learning model to input a cardiac characteristics set and output a delivery plan, the machine learning model trained based on delivery plans determined to be effective at treating arrhythmias represented by the cardiac characteristics sets. In some aspects, the techniques described herein relate to a method further including receiving a patient cardiac characteristic set and applying the trained machine learning model to a patient cardiac characteristics set of a patient with an arrhythmia to identify an delivery plan for treating the arrhythmia.

In some aspects, the techniques described herein relate to a method performed by one or more computing systems for identifying a delivery plan for a patient, the method including: accessing a patient cardiogram of a patient; accessing a library that associates simulated cardiograms with delivery plans determined to be effective at treating a patient with an arrhythmia represented by that simulated cardiogram, the delivery plans determined to be effective by running lesion development simulations and lesion evaluation simulations for combinations of cardiac characteristic set that represent an arrhythmia; based on the library, identifying a delivery plan associated with a simulated cardiogram that is similar to patient cardiogram; and outputting an indication of the identified delivery plan. In some aspects, the techniques described herein relate to a method wherein the identifying is performed with a machine learning model trained based on the associations of simulated cardiograms with delivery plans.

In some aspects, the techniques described herein relate to a method performed by one or more computing systems for identifying a delivery plan for a patient with an arrhythmia, the method including: accessing a patient cardiac characteristics set of a patient; accessing a library that associates cardiac characteristics sets with delivery plans, each delivery plan being determined to be effective at treating an arrhythmia patients having those cardiac characteristics; based on the library, identifying a delivery plan associated with a simulated cardiogram that is similar to patient cardiogram; and outputting an indication of the identified delivery plan. In some aspects, the techniques described herein relate to a method wherein the identifying is performed with a machine learning model trained based on the associations of cardiac characteristics sets with delivery plans. In some aspects, the techniques described herein relate to a method wherein the machine learning model is a neural network. In some aspects, the techniques described herein relate to a method wherein the machine learning model is as transformer. In some aspects, the techniques described herein relate to a method wherein a delivery plan is determined to be effective by running lesion development simulations and lesion evaluation simulations for combinations of cardiac characteristics set that represent arrhythmias.

In some aspects, the techniques described herein relate to a method performed by one or more computing systems for evaluating effectiveness of a lesion for treating an arrhythmia, the method including: accessing lesion characteristics of the lesion; running a lesion evaluation simulation based on a cardiac characteristics set and the lesion characteristics, the cardiac characteristics set based on cardiac tissue characteristics of an arrhythmia adjusted based on the lesion characteristics; based on a lesion effectiveness criterion being satisfied based on the lesion evaluation simulation, identifying a delivery plan and an associated lesion characteristics based on the lesion characteristic and the associated lesion characteristics satisfying a lesion similarity criterion; and outputting an indication of the identified delivery plan.

In some aspects, the techniques described herein relate to one or more computing systems including: one or more computer-readable storage mediums that store computer-executable instructions for controlling the one or more computing systems to: run a lesion development simulation to simulate the effect of a delivery plan on cardiac tissue, the effect including formation of a lesion having lesion characteristics; run a lesion evaluation simulation of electrical activity of a heart based on a cardiac characteristics set, the cardiac characteristics set based on an arrhythmia cardiac tissue characteristics set adjusted based on the lesion characteristics; and determine whether the lesion evaluation simulation results in an arrhythmia improvement; and one or more processors for controlling the one or more computing systems to execute one or more of the computer-executable instructions.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. A method for treating an arrhythmia of a patient, the method comprising:

under control of one or more computing systems:

running a lesion development simulation based on cardiac characteristics and a treatment plan that specifies a delivery plan and a target location to generate a simulated lesion having lesion characteristics;

initializing a three-dimensional (3D) mesh representing a heart based on the cardiac characteristics, vertices of the 3D mesh associated with cardiac tissue characteristics, one or more vertices associated with cardiac tissue characteristics representing an arrhythmia source;

adjusting the cardiac tissue characteristics of at least some of the vertices of the 3D mesh to reflect an effect of an ablation resulting in formation of the simulated lesion; and running a lesion evaluation simulation based on the 3D mesh with the adjusted cardiac tissue characteristics to determine whether the simulated lesion would be effective at treating the arrhythmia of the patient; and performing an ablation on the patient based on the delivery plan and the target location and based on the determination as to whether the simulated lesion would be effective at treating the arrhythmia of the patient.

2. The method of claim 1 wherein the delivery plan specifies a delivery plan duration and an electrode activation plan, the electrode activation plan specifying voltage and a voltage duration for each electrode of an ablation device.

3. The method of claim 2 wherein the cardiac characteristics include electrical conductivity and the lesion development simulation is based on an electric field generated by voltages and voltage durations of the electrode activation plan.

4. The method of claim 3 wherein the lesion development simulation simulates electroporation of cardiac tissue.

5. The method of claim 3 wherein the lesion development simulation simulates an effect of the electric field on transmembrane potential of cardiac tissue.

6. The method of claim 5 wherein the transmembrane potential is based on cardiac tissue characteristics that include conductivity and permittivity.

7. The method of claim 3 wherein the lesion development simulation simulates an effect of heat on cardiac tissue and blood.

8. The method of claim 3 wherein the lesion development simulation simulates an effect of electrode pressure on a heart wall and electrode angle relative to the heart wall.

9. The method of claim 1 wherein the 3D mesh is based on cardiac geometry of the heart of the patient and the cardiac tissue characteristics are derived from the heart of the patient.

10. The method of claim 1 further comprising, under control of the one or more computing systems, prior to adjusting the cardiac tissue characteristics, running an arrhythmia simulation of electrical activity of the heart represented by the 3D mesh based on the cardiac tissue characteristics until the electrical activity is consistent with an arrhythmia.

11. The method of claim 1 wherein running of the lesion development simulation simulates a pulsed field ablation.

12. The method of claim 1 wherein running of the lesion development simulation simulates a radiofrequency ablation.

13. The method of claim 1 further comprising, under control of the one or more computing systems, for each of a plurality of sets of cardiac characteristics, performing the initializing of a 3D mesh and for each of a plurality of treatment plans, performing the running of a lesion development simulation based on that treatment plan, the adjusting of cardiac tissue characteristics, and the running a lesion evaluation simulation.

14. The method of claim 13 further comprising, under control of the one or more computing systems, training a machine learning model using training data that includes for each combination of a set of cardiac characteristics and treatment plans, generating a training data set that includes at least one feature derived from those cardiac characteristics, and one or more labels indicating that treatment plan and effectiveness of the simulated lesion developed based on that treatment plan.

15. The method of claim 14 further comprising, under control of the one or more computing systems, applying the trained machine learning model to at least one feature derived from cardiac characteristics of the patient to generate an indication of a treatment plan that may be effective at treating the patient.

16. A method for treating an arrhythmia of a patient, the method comprising:

accessing one or more computing systems having one or more computer-readable storage mediums that store computer-executable instructions for controlling the one or more computing systems to:

run a lesion development simulation based on cardiac characteristics and a treatment plan that specifies a delivery plan and a target location to generate a simulated lesion having lesion characteristics; and run a lesion evaluation simulation to determine whether the simulated lesion would be effective at treating the arrhythmia of the patient; and one or more processors for controlling the one or more computing systems to execute one or more of the computer-executable instructions; and performing an ablation on the patient based on the treatment plan based on the determination as to whether the simulated lesion would be effective at treating the arrhythmia of the patient.

17. The method of claim 16 wherein the computer-executable instructions further control the one or more computing systems to, prior to running the lesion development simulation, run an arrhythmia simulation of electrical activity until the electrical activity is consistent with an arrhythmia.

18. The method of claim 16 wherein the lesion evaluation simulation is based on a three-dimensional (3D) mesh representing a heart, the 3D mesh having vertices associated with cardiac tissue characteristics representing the simulated lesion.

19. The method of claim 16 wherein the lesion development simulation simulates electroporation of cardiac tissue.

20. The method of claim 16 wherein the lesion evaluation simulation simulates electrical activity of a heart having the simulated lesion.

* * * * *